(12) United States Patent
Cingotti

(10) Patent No.: US 6,190,687 B1
(45) Date of Patent: Feb. 20, 2001

(54) METHOD FOR PREPARING AN EXTRACT OF ACTIVE PRINCIPLES IN THE FORM OF MICROGRANULES BASED ON DIETARY FIBERS

(75) Inventor: Dominique Cingotti, Villeurbanne (FR)

(73) Assignee: Vegetalys Corporation, Tortola (VG)

( * ) Notice: Under 35 U.S.C. 154(b), the term of this patent shall be extended for 0 days.

(21) Appl. No.: 09/463,117

(22) PCT Filed: Jul. 23, 1998

(86) PCT No.: PCT/FR98/01634

§ 371 Date: Jan. 18, 2000

§ 102(e) Date: Jan. 18, 2000

(87) PCT Pub. No.: WO99/06028

PCT Pub. Date: Feb. 11, 1999

(30) Foreign Application Priority Data

Jul. 31, 1997 (FR) .................................. 97/10041

(51) Int. Cl.⁷ ................................ A61K 9/16; A61K 9/50
(52) U.S. Cl. .......................... 424/439; 424/489; 424/490; 424/499; 424/195.1; 427/213.31
(58) Field of Search .................................. 424/417, 418, 424/493, 489, 490, 497, 499, 195.1; 514/952, 23; 427/497

(56) References Cited

U.S. PATENT DOCUMENTS 5,275,824 * 1/1994 Carli et al. ........................... 424/490

FOREIGN PATENT DOCUMENTS

| 0 498 463 | 8/1992 | (EP) . |
| 0 524 484 | 1/1993 | (EP) . |
| 0 686 399 | 12/1995 | (EP) . |
| 2041220 | 9/1980 | (GB) . |

* cited by examiner

Primary Examiner—Thurman K. Page
Assistant Examiner—Liliana Di Nola-Baron
(74) Attorney, Agent, or Firm—Wall Marjama & Bilinski

(57) ABSTRACT

A method of preparing an extract of at least one active principle in the form of completely dry soluble granules wherein an extract of an active principle is prepared in a solvent medium and depositing the extract upon the internal and external walls of microporous carriers that are insoluble in the solvent, drying the impregnated granules, and coating the walls of the granules with a film forming polymer. The granules are a soluble dietary fiber based upon a polymer selected from the group comprising inulin and oligofructoses and, fructo-oligosaccharides separately or mixed.

11 Claims, No Drawings

METHOD FOR PREPARING AN EXTRACT OF ACTIVE PRINCIPLES IN THE FORM OF MICROGRANULES BASED ON DIETARY FIBERS

BACKGROUND OF THE INVENTION

The invention relates to a new method for preparing completely soluble microgranules prepared from extracts or solutions of active principles; these microgranules are intended to be used as they are for the reconstitution of solutions or to be incorporated into various galenic forms.

The administration and the use of extracts of active principles, especially of natural origin, in the form of Essential Oils, of solvent extraction solutions pose problems at various levels during use:

incomplete dissolution difficulty of precise proportioning masking of taste inappropriate galenic presentation The production, in dry form, of these different extracts of active principles involves, for the majority, methods using a substantial supply of heat; nebulization-spray-drying, evaporation under vacuum or otherwise, recovery from grinding or micronization, these various operations being capable of causing substantial adverse modifications. The dry forms of these various extracts which are thus obtained are subjected to adverse modifications of active principles which are linked to high hygroscopicity due to the increases in specific surface area by the physical treatments cited.

There has for example been proposed in the document EP-A-0,524,484 a powder for preparing instant drinks which is obtained by aqueous dissolution of tea extracts and of an inulin carrier, the mixture then being dried, and then spray-dried.

Even if a low-calorie composition is obtained by virtue of the degradation of the carrier into fructose units, its preparation requires a large volume of inulin for a given quantity of extract, which contributes towards increasing the cost of the formulation. In addition, the thermal energy released during the phase for spray-drying the powder once the active principle is attached to the inulin leads to the said active principle being thermally degraded, which excludes the use of heat-sensitive active principles. Moreover, the method used excludes the incorporation of any water-insoluble substance, in particular volatile substances, in particular flavourings and essential oils, which will be partially or completely evaporated during the spray-drying process.

SUMMARY OF THE INVENTION

The problem which the invention proposes to solve is therefore to develop a method for the manufacture of an extract of active principle of reduced cost by seeking to optimize the proportions of each of the constituents.

Another objective of the invention is to provide stability over time to the manufactured preparation by using a method free of thermal degradation which makes it possible to incorporate active principles or extracted substances which are heat-sensitive.

The aim of the invention is also to provide a method for the manufacture of an extract of active principle in which the choice of solvent is not limiting, which thus makes it possible to use any type of active principle independently of its physicochemical characteristics.

DESCRIPTION OF THE INVENTION

To solve all of these problems, the invention provides a method for the preparation of an extract of at least one active principle in the form of completely soluble dry granules, which consists:

first, in preparing an extract of an active principle in a solvent medium;

then, in depositing this extract on the internal and external walls of a microporous carrier insoluble in the solvent medium, provided in the form of microgranules, having a specific surface area of at least 0.50 m$^2$/g;

and in drying the impregnated granular carrier obtained;

then, in coating the impregnated walls of the microporous carrier with a film-forming polymer; characterized in that the microporous carrier is a soluble dietary fibre based on a polymer selected from the group comprising inulin and oligofructoses and fructo-oligosaccharides, on their own or mixed.

In other words, the invention consists:

in a first instance, in preparing extracts of plant, animal or other origin, or solutions of active principles;

in a second instance, in impregnating the microgranules whose specific surface area of at least 0.50 m$^2$/g provides optimum impregnation, these microgranules being insoluble in the extracts or solutions of active principles;

in a third instance, in evaporating the solvent by drying, the substances in the extract or the solution of active principles remaining absorbed in the microscopic structure of the microgranular carrier;

and finally, in coating the microgranule obtained with a film of polymers allowing it to offer stability over time inside the galenic form which will carry it during its administration, and also to be able to offer gradual release of the active principles retained, through the film of polymers.

In the description and in the claims, "extracts or solutions of active principles" should be understood to mean any form of solution containing active principles of plant, animal or other origin, such as solutions of synthetic active principles or active principles of inorganic origin (trace elements and the like), maceration liquids, essential oils, gums, resins. These extracts are prepared in a known manner, in particular in a solvent medium appropriate for the desired active principles, or by a specific physical method, that is to say respectively ethanol for the extract, or steam distillation (essential oils, volatile substances). Depending on the active principles, there is used as solvent a solvent which solubilizes the said active principles and which preserves the structure of the microgranular carrier, and which is not toxic. In practice, ethanol is used. It is possible to add adjuvants to the extract or to the solution of active principles with the aim of facilitating the dissolution or the dispersion of the active principles during the manufacture, or of providing mechanical protection of the final product.

In the description and in the claims, "dietary fibres" designate any compound from plant cells which is resistant to the various enzymatic hydrolyses used during the physiological process of digestion. These fibres are composed of cellulose, hemicellulose, oligosaccharides, pectin, gums, waxes and lignin; these various compounds are those taken into account in the analyses of dietary fibres.

In practice:

the active principle is an extract of plants or of a portion of plants;

the solvent medium consists of a solvent from the group comprising water, ethanol, acetone, dichloromethane;

the microporous carrier is a microgranule obtained by spray-drying or by wet granulation;

the spray-dried microgranule is based on soluble fibres which can be combined with other substances such as polyalcohols (sorbitol, xylitol, mannitol), polyols (maltodextrins and the like), or fatty substances;

the extract is deposited on the walls by wet granulation and the drying is carried out with hot air;

the film-forming polymer is a compound which is soluble in the gastrosoluble (hydroxypropylmethylcellulose) or gastro-resistant (hydroxypropylmethylcellulose phthalate) digestive system;

the film-forming polymer is pulverized in a turbine or in a fluidized bed.

Once this extract or solution of active principles has been prepared in a known manner, the microgranule is prepared by the technique of spray-drying or wet granulation which makes it possible to obtain a microgranular carrier having a porous structure which is quantified by its specific surface area: unit of surface area/unit of mass; generally, there are used as dietary fibres soluble fibres such as inulin and oligofructoses which are natural plant substances allowing the storage of carbohydrates in various plants which are used for human consumption, such as leek, onion, wheat, garlic, chicory, artichoke and the like.

According to a first embodiment of the invention, the microgranular carrier is a powder based on inulin obtained by extraction from chicory roots and from any other multi-rich plant.

Inulin is a mixture of oligomers and of polymers of fructose, whose structure is represented by the formula GFn, in which:

G: glucosyl unit

F: fructosyl unit n: number of bound fructosyl units (n greater than 2)

DP: degree of polymerization varying from 2 to 60

Bond of the $\beta(1-2)$ type

According to a second embodiment of the invention, the microgranular carrier is a powder based on oligofructoses obtained by hydrolysis of inulin. Likewise, the oligofructoses and fructo-oligosaccharides may be obtained by synthesis.

The oligofructoses or fructo-oligosaccharides are a mixture of oligomers and of polymers of fructose, whose structure is represented by the formula GFn or Fm, in which:

G: glucosyl unit

F: fructosyl unit n and m: number of bound fructosyl units (n greater than 2)

DP: degree of polymerization varying from 2 to 20

The oligofructoses contain molecules of the GFn type and of the Fm type

Bond of the $\beta(1-2)$ type

The specific surface area of the microgranule should be at least greater than or equal to 0.50 m²/gram of carrier.

This microgranular porous carrier is well known and widely used, such that it is available in a ready-for-use form.

It is possible to add other substances prepared in the form of microgranules by the same spray-drying technique as the above fibres:

sugars derivatives of sugars: ester hydrolysates, alcohols, and the like lipophilic derivatives, waxes, polymers, and the like polysaccharides and hydrolysates proteins The specific surface area of the microgranule should be at least greater than or equal to 0.50 m²/g of carrier.

This microgranular porous carrier is well known and is widely used, which means that it can be found in a form ready for use.

The deposition is carried out under normal temperature and pressure conditions, in a conventional mixer/granulator (of the planetary, ribbon or ploughshare type) or a fluidized bed granulator. The microgranular carrier is first placed inside the mixer and moistened with the extract at the rate of 1% to 60% of the mass. Indeed, if the volume of the extract exceeds this 60% limit, a suspension of microgranules is obtained, the structure of the microgranule no longer being able to absorb the extract.

Once the carrier has been impregnated up to a maximum of 60%, the impregnated carrier is dried in a ventilated atmosphere, at medium temperature, for example 50° C., with recycling and optional recovery of solvent. It should be noted that if a fluidized bed granulator is used, the impregnation and the drying of the carrier are performed simultaneously. Once the drying is complete, the microgranule is sized so as to remove the particles below the mean size.

Once the microgranules have been obtained and for reasons of preservation, administration and release of the active principles in the body, these microgranules may be subjected to an additional operation of coating with a film of polymers, using conventional means (turbine, fluidized bed and the like).

The principal film-forming polymers for coating may be classified, according to their solubility and the bioavailability which they offer the coated microgranules, into gastrosoluble polymers (hydroxypropylcellulose and the like), gastroresistant polymers (cellulose acetyl phthalate, hydroxypropylcellulose phthalate and the like), and insoluble polymers (ethyl cellulose and the like) which allow the production of prolonged-release coatings. These film-forming polymers are generally used in organic medium, although in each category of polymers, some of them are also used in aqueous medium when the microgranular carrier allows it. The coating is carried out using the chosen solution of polymers into which there have been incorporated, if necessary, additives such as plasticizers and fillers which are commonly used:

lubricants, opacifiers colouring pigments

Advantageously, the quantity of microgranular carrier can absorb 5 to 60% by volume of coating solution relative to 100% of the weight of the carrier, knowing that the coating solution composed of extracts or of a solution of active principles may contain p.p.m. values at 20% of dry residue. On the other hand, when the volume/weight ratio exceeds 60%, destruction of the microgranular carrier and a loss of dry residue are noted. Indeed, as the solution cannot be absorbed by the microgranular carrier, the solution and a fortiori its dry residue remain on the walls of the apparatus with a loss of active agents on the final product and with drying difficulties in the method. As already stated, excellent results are obtained with proportions of 5 to 60% by volume of solution of coating relative to 100% of the weight of excipient, that is to say 5 ml to 60 ml of coating solution per 100 g of microgranular excipient.

As microgranular carrier, use is preferably made of soluble dietary fibres which may be combined with substances of the polyalcohol, gum, mucilage, resin or protein type, and the like, obtained by nebulization giving a specific surface area per unit of weight necessary. This type of operation gives the carrier a capacity for absorption with respect to the solution of extracts or of active principles, and ensures, after removal of the solvent from the solution, retention of its dry residue (containing the active agents) in the structure of the microgranular carrier. These absorbed microgranules may be dissolved as they are, or may be integrated into various galenic forms, gelatin capsules, tablets, continuous pasty forms (hydrophilic-lipophilic) or emulsions and the like.

The use of the soluble dietary fibres makes it possible to exploit their intrinsic characteristics, which are:

Inulin and the oligofructoses which are dietary fibres are not significantly hydrolysed during passage through acidic medium in the stomach. The enzymes in the body which are present in the small intestine, of the sucrase-maltase type, abundantly present in the intestine, have no hydrolytic action on the bonds of the units forming these fibres, causing no increase in glycaemia and in the level of insulin in the blood. As such, these fibres may be used in the diet intended for diabetics.

Inulin and the oligofructoses are rapidly fermented by the intestinal flora in the colon. The carbohydrates are metabolized to fatty acids with a small number of carbons (propionic acid, lactic acid, butyric acid and the like), and to a gas.

The use of soluble dietary fibres as carrier, whose degradation predominantly occurs during the final phase of digestion, in the large intestine and the colon, because of the resistance of the fibres to enzymatic hydrolysis, has the following advantages:

The process of controlled disintegration, fibres metabolized "in fine", makes it possible to obtain an active principle-fibre bond which is present throughout the course of digestive assimilation, strengthened by the coating of polymer films, thus offering increased bioavailability, and specific.

Low calorific value: inulin 1.0 kcal/g against 4.0 kcal/g for carbohydrates inulin 1.0 kcal/g against 2.40 kcal/g for polyols oligofructose 1.5 kcal/g against 4.0 kcal/g for carbohydrates oligofructose 1.5 kcal/g against 2.40 kcal/g for polyols The low degradation of these fibres, providing no glycaemic and insulin response in the blood, makes these fibres a specific carrier in the diet intended for diabetic pathologies.

Stimulation of bifidus: the degradation of the fibres in the colon stimulates the metabolism of bifidobacteria.

Microgranules are therefore obtained which can be used in various galenic forms, which have a cross-linked structure correlated by their specific surface area/unit of weight, this cross-linked network being covered by the dry residue or the active principles which were present in the solution absorbed. The said absorbed microgranules may be coated with a film of polymers, providing specific properties of stability, solubility and bioavailability.

The manner in which the invention can be carried out and the advantages resulting therefrom will emerge more clearly from the following exemplary embodiments.

EXAMPLE No. 1

Preparation of a Completely Soluble Phytotherapeutic Drink for Slimming.

In a known manner, an alcoholic extract of fucus-ash tree-rosemary is prepared by maceration in 80% ethanol.

After the maceration time (for example 3 weeks), the medium is drawn off, drained and filtered. This aqueous-alcoholic extract has a rough composition per 100 ml:

| Total polyphenols: | 0.80 g |
| Iodine | 3.00 mg |
| Mucilages | 0.10 g |

Two microgranular carriers are prepared so as to obtain a specific surface area greater than 0.5 m$^2$/gram by nebulization (during nebulization, it may be necessary to perform microgranulation).

1st carrier obtained by spray-drying a solution of inulin at 95% (it is possible to use a ready-for-use inulin carrier obtained in the same manner: RAFTILINE GR (ORAFTI) with a mean particle size of 0.30 mm)

2nd carrier obtained by spray-drying a solution of sorbitol (it is possible to use a ready-for-use sorbitol carrier obtained in the same manner: SORBITOL INSTANT (MERCK) with a mean particle size of 0.50 mm).

These microgranules are placed at the rate of 75% inulin and 25% sorbitol in a mixer at room temperature, and the granulation of the microgranules is carried out with the solution of extract, at the rate of 50% of the mass (50 ml/100 g) and guar gum is incorporated at 2.50%.

The microgranule thus impregnated is dried in an oven at 40° C.; green microgranules carrying the dry extract are obtained after drying. They are then sized so as to re-establish the initial particle size distribution.

Microgranules of inulin and sorbitol are therefore obtained whose internal cavities and external surface are coated with the dry extract of the alcoholic solution obtained by maceration, and guar gum. The said guar gum, incorporated during granulation, sticks to the inside of the internal cavities and to the surface of the microgranule.

The microgranules obtained are then coated by spraying a solution (at 10%) of cellulose acetyl phthalate in dichloromethane; the spraying is done in a turbine with spraying of hot air, ensuring the formation of the film. The said film is soluble at a pH>5, corresponding to the conditions for dissolution during use.

The microgranules thus obtained make it possible to reconstitute a form which dissolves instantly, for the preparation of a drink intended for slimming. A galenic form is therefore obtained which is equivalent to an infusion made with the same plant species and which has the following advantages:

Microgranules coated with film, offering protection and stability to the active principles during storage Instant dissolution Preparation of the drink: cold water or hot water, preserving the same active principles in terms of quantity and quality Attractive commercial presentation This example is repeated, modifying the 2nd carrier cited above:

2nd carrier obtained by spray-drying a solution of maltodextrin (it is possible to use a ready-for-use maltodextrin carrier obtained in the same manner: GLUCIDEX IT 19 (ROQUETTE) with a mean particle size of 0.30 mm);

under the same conditions as above, a microgranule having the same characteristics is obtained.

EXAMPLE No. 2

Preparation of a Completely Soluble Phytotherapeutic Drink Intended as a Laxative.

In a known manner, an alcoholic extract (A) of a mixture of plants: liquorice-anise-rosemary, is prepared by maceration in 96% ethanol.

After the same maceration time as in Example 1, this alcoholic extract, which will provide the flavouring, is drawn off, drained and filtered.

In a known manner, an aqueous extract of senna leaves (B) is prepared so as to extract the active principles (sennosides: on average above 2.6% in the leaves). Upon boiling under reflux, the extract obtained is drawn off, drained and concentrated under vacuum so as to obtain extracts whose ratio: weight of plant/concentrated extract varies from 1/1 to 1/8. By assaying the sennosides during different phases of concentration, it is ensured that no degradation of the said active principles is observed, their quantity being in proportion with the concentration ratios during the method.

Two microgranular carriers are prepared so as to obtain a specific surface area greater than 0.5 m$^2$/gram by nebulization (during nebulization, it may be necessary to perform microgranulation)

1st carrier obtained by spray-drying a solution of inulin at 95% (it is possible to use a ready-for-use inulin carrier obtained in the same manner: RAFTILINE GR (ORAFTI) with a mean particle size of 0.30 mm)

2nd carrier obtained by spray-drying a solution of oligofructose at 95% (it is possible to use a ready-for-use oligofructose carrier obtained in the same manner: RAFTILOSE P 95 (ORAFTI) with a mean particle size of 0.30 mm).

These microgranules are placed at the rate of 75% inulin and 25% oligofructose in a mixer at room temperature. The granulation of the microgranules is carried out with the mixture of extracts (A+B: this A+B mixture is composed of 30% of A and 70% of B), at the rate of 50% of the mass, that is to say 50 ml of A+B per 100 g of microgranules.

The microgranule thus impregnated is dried in an oven at 40° C. Green microgranules carrying the dry extract are obtained after drying. They are then sized so as to re-establish the initial particle size distribution.

Microgranules of inulin and oligofructose are therefore obtained whose superficial internal cavities are coated with the dry extract of the alcoholic solution obtained by maceration, and with the concentrated aqueous extract of SENNA.

The microgranules are coated in the same manner and with the same film-forming component as in Example No. 1.

The microgranules thus obtained make it possible to reconstitute a form which dissolves instantly without deposition, for the preparation of a drink intended as a laxative. A galenic form is therefore obtained which is equivalent to an infusion prepared with the same plant species, and which has the following advantages:

Instant dissolution

Preparation of the drink: cold water or hot water, preserving the same active principles in terms of quantity and quality Attractive commercial presentation

EXAMPLE No. 3

Antisun Milk

Example No. 1 is repeated using not a multiplant extract but a maceration, in 80% alcohol, of Centella asiatica which possesses cicatrizing and stimulating properties. The manufacture of the extract is carried out using 80% ethyl alcohol which is specific for the extraction of the terpenic derivatives responsible for the pharmacological activity. The alcoholic extract form as such is difficult to incorporate into an emulsion, and its use by the local route as it is or in the form of an emulsion gives rise to major algetic phenomena.

The same proportions of constituents are used as in Example No. 1.

Green microgranules are thus obtained possessing the active principles (terpenic derivatives) and thus free of extraction solvent and therefore of its disadvantages on the formulation and on the use by the local route.

The coating with a film is carried out in the same manner as in Example No. 1.

These microgranules can be incorporated into an emulsion intended for restructuring dermatology for the skin, in the form of an antisun milk of formula:

| FATTY PHASE: | |
| --- | --- |
| emulsifier B6 | 5% |
| paraffin oil | 8% |
| isopropyl myristate | 4% |
| *Meleleuca alternifolia* essential oil | 2% |
| *Rosa rubiginosa* essential oil | 2.50% |
| AQUEOUS PHASE | |
| preservative Fondix | 1% |
| qs to | 100% |

The two phases are heated to 65° C. and incorporated into a mixer-emulsifier. At 50° C., the emulsion is prepared in the mixer by incorporating the previously prepared microgranules in a proportion ranging from 1 to 20% depending on the content of terpenic derivatives to be obtained. The microgranules dissolve instantly, the different active principles then being distributed independently in the phases of the emulsion according to their chemical affinity.

An antisun milk with a guaranteed content of active principles is obtained without incorporating the specific solvent which was removed during the preparation of the microgranule.

EXAMPLE No. 4

Antisun Milk

Example No. 3 is repeated using, as extract, a maceration, in 80% alcohol, of Calendula officinalis, allowing optimum extraction of the compounds: flavonoids, saponins, carotenoids, which confer on Calendula officinalis emollient, antiseptic and anti-inflammatory properties.

The microgranules absorbed by the Calendula officinalis extract are incorporated in the same manner into a milk formula, as in Example No. 3.

EXAMPLE No. 5

Microgranules Carrying Essential Oils

A solution of Essential oils in 95% ethanol is prepared at the rate of:

| Lavender Essential Oil | 6.0% |
| --- | --- |
| Rosemary Essential Oil | 1.5% |
| Thyme Essential Oil | 1.0% |

Two microgranular carriers are prepared so as to obtain a specific surface area greater than 0.5 m$^2$/gram by nebulization (during nebulization, it may be necessary to perform microgranulation):

1st carrier obtained by spray-drying a solution of inulin at 95% (it is possible to use a ready-for-use inulin carrier obtained in the same manner: RAFTILINE GR (ORAFTI) with a mean particle size of 0.30 mm)

2nd carrier obtained by spray-drying a solution of oligofructose at 95% (it is possible to use a ready-for-use oligofructose carrier obtained in the same manner: ACTILIGHT (BEGHIN SAY) with a mean particle size of 0.30 mm).

These microgranules containing 75% inulin and 25% oligofructose are treated in an identical manner to Examples 1 to 3 with the aid of the solution at the rate of 50% by volume per 100% by mass of microgranules, and coated with the film-forming agent as in the preceding examples. Microgranules with a strong aromatic odour are obtained.

The presence of the terpenic derivatives (tracers) in the starting essential oils present in the solution is compared, qualitatively by Gas Chromatography (GC), to those present in the microgranules (the essential oils of 10 grams of microgranules are extracted with 15 ml of methanol). The terpenic derivatives chosen for the qualitative GC analysis are, from the most volatile to the least volatile:

Alpha-pinene

Beta-pinene

Limonene

Cineole

Para-cymene

Camphor

Linalol

Linalyl acetate

Alpha-terpineol

Thymol

The chromatograms of the starting solution and of the microgranules are similar; the most volatile components of the essential oils ($\alpha$-pinene and $\beta$-pinene) are found on the microgranules, demonstrating that this method makes it possible to retain the volatile fractions of the essential oils.

EXAMPLE No. 6

Coated Microgranules Carrying Lemon Essential Oil

An essential oil-based solution is prepared as follows:

| | |
|---|---|
| lemon essential oil | 40% |
| polyvinylpyrrolidone | 1% |
| polysorbate 60 | 1% |
| ethanol, 96%, qs | 100% |

Example No. 5 is repeated, light yellow microgranules with a strong aromatic odour are obtained.

These microgranules are subjected to a coating operation with a film-forming substance (cellulose acetophthalate). The coating solution is composed of:

| | |
|---|---|
| Cellulose acetophthalate | 10% |
| acetone | 20% |
| Ethyl alcohol | 70% |

The coating is carried out by spraying in a turbine by a conventional method.

A microgranule, soluble at a pH>5.8, is obtained which is instantly soluble in water, and which can thus be incorporated into various formulations for flavouring:

Preparation for drinks

Dry forms: flavouring of tablets, powders

Infusions

Etc. . . .

EXAMPLE No. 7

Microgranules Coated with Gastroresistant Film, Carrying Thyme Essential Oil.

Example No. 5 is repeated with a solution based on thyme essential oil. The microgranules are then coated by the same method as in Example No. 5, with the following polymer solution:

| | |
|---|---|
| hydroxypropylcellulose phthalate HP 50 | 10% |
| isopropanol | 45% |
| ethyl acetate | 45% |

The microgranules obtained after coating have a pH>5.0, hence their incorporation into forms per os, in gelatin capsules.

EXAMPLE No. 8

Microgranules with Insoluble Coating for Incorporation into a Slimming Gel.

Example No. 7 is repeated with the following solution:

| | |
|---|---|
| alcoholic extract of guarana with a defined caffeine titre | 20% |
| alcoholic extract of ivy | 20% |
| alcoholic extract of fucus | 20% |
| ethyl alcohol, 95%, qs | 100% |

Absorbed microgranules are manufactured by incorporation of 50% of the solution of extract into the microgranular carrier obtained as in Example No. 1, and comprising:

1st carrier obtained by spray-drying a solution of inulin at 95% (it is possible to use a ready-for-use inulin carrier obtained in the same manner: RAFTILINE GR (ORAFTI) with a mean particle size of 0.30 mm)

2nd carrier obtained by spray-drying a solution of sorbitol (it is possible to use a ready-for-use sorbitol carrier obtained in the same manner: SORBITOL INSTANT (MERCK) with a mean particle size of 0.50 mm);

3rd carrier (vitamin E—MICROGRANULES MERCK), obtained by spray-drying.

The microgranules are coated by the same method as in Example No. 7, with the following insoluble polymer solution:

| | |
|---|---|
| ethyl cellulose | 10% |
| diethyl phthalate | 2% |
| ethyl alcohol 95% | 44% |
| methylene chloride | 44% |

These microgranules are incorporated into a gel of conventional acrylic resin known as CARBOPOL 940, at the rate of 2 to 10%, so as to obtain a massage gel where the microgranules carry active agents protected by a coating with a film of polymers, these active agents being released by the rubbing due to the massage, which breaks the film and dissolves the active agents which are released.

EXAMPLE No. 9

Microgranules for use as Slimming Appetite-Suppressant Drink

Example No. 8 is repeated with the following solution:

| | |
|---|---|
| dry extract of *Garcinia cambodgia* | 30% |
| dry extract of *Gymnema sylvestris* | 15% |
| chitin | 15% |
| ethyl alcohol, 95%, qs | 100% |

Absorbed microgranules are manufactured by incorporation of 20% of the solution of extract into the microgranular carrier obtained as in Example No. 1, and comprising:

1st carrier (63%) obtained by spray-drying a solution of inulin at 95% (it is possible to use a ready-for-use inulin carrier obtained in the same manner: RAFTILINE GR (ORAFTI) with a mean particle size of 0.30 mm) 2nd carrier (25%): polysaccharide (glucomannan), extract of Amorphophalus konjac root.

Microgranules of inulin are thus obtained whose internal cavities and external surface are coated with the dry extracts and the chitin of the alcoholic suspension, and the glucomannan is incorporated during the granulation, adhering inside the internal cavities and to the surface of the microgranule.

What is claimed is:

1. A method for the preparation of an extract of at least one active component in the form of completely soluble dry granules, which comprises:
    preparing an extract of an active component in a solvent medium;
    depositing said extract by wet granulation on the internal and external walls of a microporous carrier which is insoluble in said solvent medium, with said microporous carrier being in the form of microgranules made of a dietary fiber based on a polymer selected from the group consisting of any one of inulin, oligofructoses, and fructooligosaccharides, and mixtures thereof, and having a specific surface area of at least about 0.5 $m^2/g$;
    drying the impregnated granular carrier; and
    then coating the impregnated walls of the microporous carrier with a film-forming polymer.

2. Method according to claim 1, characterized in that the microporous carrier is provided in spray-dried form.

3. Method according to claim 1, characterized in that the soluble dietary fibres are combined with other substances selected from the group comprising polyalcohols, polyols and fatty substances.

4. Method according to claim 1, characterized in that the active principle is an extract of plants or of a portion of plants.

5. Method according to claim 1, characterized in that the solvent medium consists of a solvent selected from the group comprising water, ethanol, acetone and dichloromethane.

6. Method according to claim 1, characterized in that the microgranular carrier obtained is a powder based on inulin obtained by extraction from chicory roots or from any other inulin-rich plant.

7. Method according to one of claim 1, characterized in that the microgranular carrier is a powder based on oligofructoses obtained by hydrolysis of inulin.

8. Method according to claim 1, characterized in that the microgranular carrier is a powder based on oligofructoses obtained by synthesis.

9. Method according to claim 1, characterized in that the deposition of the extract on the walls is carried out by wet granulation, at the rate of 1% to 60% by volume relative to 100% by weight of the said carrier microgranules, so as to coat the internal structures with the active agents present in the solution, the drying being carried out with hot air.

10. Method according to claim 1, characterized in that the film-forming polymer is a compound soluble in the digestive system selected from the group of acidic pH, gastro-soluble compounds or basic pH, gastro-resistant compounds.

11. Method according to claim 7, characterized in that the film-forming polymer is pulverized in a turbine or in a fluidized bed.

* * * * *